United States Patent
MacDonald et al.

(10) Patent No.: US 8,702,618 B2
(45) Date of Patent: *Apr. 22, 2014

(54) VISUAL INDICATING DEVICE FOR BAD BREATH

(75) Inventors: John Gavin MacDonald, Decatur, GA (US); Kevin P. McGrath, Alpharetta, GA (US); RameshBabu Boga, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/549,550

(22) Filed: Jul. 16, 2012

(65) Prior Publication Data

US 2013/0261486 A1    Oct. 3, 2013

Related U.S. Application Data

(63) Continuation of application No. 12/134,547, filed on Jun. 6, 2008, now Pat. No. 8,221,328, which is a continuation of application No. 10/687,270, filed on Oct. 16, 2003, now Pat. No. 7,413,550.

(51) Int. Cl.
   *A61B 5/08*    (2006.01)

(52) U.S. Cl.
   USPC .......................................... 600/529; 600/530

(58) Field of Classification Search
   USPC .......................................... 600/303, 532, 300
   See application file for complete search history.

(56) References Cited

U.S. PATENT DOCUMENTS

| | | | |
|---|---|---|---|
| 2,015,864 A | 10/1935 | Müller et al. |
| 2,429,694 A | 10/1947 | King |
| 2,534,229 A | 12/1950 | Carhart et al. |
| 2,593,146 A | 4/1952 | Howard |
| 3,033,655 A | 5/1962 | Grosskopf |
| 3,193,404 A | 7/1965 | Davis |
| 3,266,973 A | 8/1966 | Crowley |
| 3,338,992 A | 8/1967 | Kinney |

(Continued)

FOREIGN PATENT DOCUMENTS

| EP | 0103214 B1 | 3/1984 |
| EP | 0232141 A1 | 8/1987 |

(Continued)

OTHER PUBLICATIONS

Abstract of Japanese Patent No. JP04255767 Sep. 10, 1992.

(Continued)

*Primary Examiner* — Michael D'Angelo
(74) *Attorney, Agent, or Firm* — Dority & Manning, P.A.

(57) ABSTRACT

The invention provides a breath testing device which includes a visual indicating agent which changes color in the presence of an odor associated with bad breath, such as sulfur and ammonia odors. An example of the visual indicating agent is 4,4'-bis(dimethylamino)-benzhydrol (Michler's hydrol or BDMB) and related dyes having a similar chemical structure. The indicating agent is applied to a substrate which is then inserted into a tube or straw, or which covers one end of a straw. When a user with bad breath blows into the tube or straw, the indicating agent will change color. The breath testing devices provide a quick and affordable means for a user to test their breath, and they may be packaged in discreet, pocket-sized dispensers which can be carried in a pocket or purse.

21 Claims, 4 Drawing Sheets

(56) References Cited

U.S. PATENT DOCUMENTS

| | | | |
|---|---|---|---|
| 3,341,394 | A | 9/1967 | Kinney |
| 3,381,688 | A | 5/1968 | Satas |
| 3,494,821 | A | 2/1970 | Evans |
| 3,502,538 | A | 3/1970 | Petersen |
| 3,502,763 | A | 3/1970 | Hartmann |
| 3,507,269 | A * | 4/1970 | Berry ........................... 600/367 |
| 3,542,615 | A | 11/1970 | Dobo et al. |
| 3,615,478 | A | 10/1971 | Hoshino et al. |
| 3,692,618 | A | 9/1972 | Dorschner et al. |
| 3,794,497 | A | 2/1974 | Pratt |
| 3,802,817 | A | 4/1974 | Matsuki et al. |
| 3,836,633 | A | 9/1974 | Beschke |
| 3,849,241 | A | 11/1974 | Butin et al. |
| 3,919,437 | A | 11/1975 | Brown et al. |
| 3,960,494 | A | 6/1976 | Verma et al. |
| 3,971,665 | A | 7/1976 | Suzuki et al. |
| 4,006,030 | A | 2/1977 | Yoshida et al. |
| 4,038,101 | A | 7/1977 | Thompson |
| 4,041,203 | A | 8/1977 | Brock et al. |
| 4,078,029 | A | 3/1978 | Yoshida et al. |
| 4,100,324 | A | 7/1978 | Anderson et al. |
| 4,101,638 | A | 7/1978 | Inoue et al. |
| 4,144,370 | A | 3/1979 | Boulton |
| 4,172,781 | A | 10/1979 | Walk et al. |
| 4,297,233 | A | 10/1981 | Gualandi |
| RE30,797 | E | 11/1981 | Davis |
| RE30,803 | E | 11/1981 | Davis |
| 4,313,820 | A | 2/1982 | Farha, Jr. et al. |
| 4,340,563 | A | 7/1982 | Appel et al. |
| 4,375,448 | A | 3/1983 | Appel et al. |
| 4,407,960 | A * | 10/1983 | Tratnyek ........................... 436/1 |
| 4,467,012 | A | 8/1984 | Pedersen et al. |
| 4,469,746 | A | 9/1984 | Weisman et al. |
| 4,488,969 | A | 12/1984 | Hou |
| 4,494,278 | A | 1/1985 | Kroyer et al. |
| 4,494,629 | A | 1/1985 | Raeburn |
| 4,517,308 | A | 5/1985 | Ehlenz et al. |
| 4,522,203 | A | 6/1985 | Mays |
| 4,525,410 | A | 6/1985 | Hagiwara et al. |
| 4,548,906 | A | 10/1985 | Sekikawa et al. |
| 4,575,556 | A | 3/1986 | Byrne et al. |
| 4,604,313 | A | 8/1986 | McFarland et al. |
| 4,640,810 | A | 2/1987 | Laursent et al. |
| 4,643,801 | A | 2/1987 | Johnson |
| 4,655,757 | A | 4/1987 | McFarland et al. |
| 4,701,218 | A | 10/1987 | Barker et al. |
| 4,715,983 | A | 12/1987 | Ota et al. |
| 4,725,415 | A | 2/1988 | Kidd |
| 4,734,324 | A | 3/1988 | Hill |
| RE32,649 | E | 4/1988 | Brandt et al. |
| 4,769,216 | A | 9/1988 | Chandler et al. |
| 4,775,585 | A | 10/1988 | Hagiwara et al. |
| 4,777,018 | A | 10/1988 | Auchincloss |
| 4,780,448 | A | 10/1988 | Broecker et al. |
| 4,781,858 | A | 11/1988 | Mizukami et al. |
| 4,783,220 | A | 11/1988 | Gamble et al. |
| 4,798,603 | A | 1/1989 | Meyer et al. |
| 4,802,473 | A | 2/1989 | Hubbard et al. |
| 4,804,630 | A | 2/1989 | Bhattacharjee |
| 4,818,464 | A | 4/1989 | Lau |
| 4,823,404 | A | 4/1989 | Morell et al. |
| 4,823,803 | A | 4/1989 | Nakamura |
| 4,844,867 | A | 7/1989 | Bäther |
| 4,853,186 | A | 8/1989 | Mura et al. |
| 4,854,332 | A * | 8/1989 | Hanakura ........................... 131/365 |
| 4,904,304 | A | 2/1990 | Watanabe et al. |
| 4,947,861 | A | 8/1990 | Hamilton |
| 4,969,457 | A | 11/1990 | Hubbard et al. |
| 4,978,615 | A | 12/1990 | Aoyama et al. |
| 4,988,505 | A | 1/1991 | Watanabe et al. |
| 5,000,746 | A | 3/1991 | Meiss |
| 5,020,533 | A | 6/1991 | Hubbard et al. |
| 5,057,302 | A | 10/1991 | Johnson et al. |
| 5,064,473 | A | 11/1991 | Kubo et al. |
| 5,094,962 | A | 3/1992 | Snyder et al. |
| 5,100,581 | A | 3/1992 | Watanabe et al. |
| 5,100,702 | A | 3/1992 | Maeda et al. |
| 5,108,739 | A | 4/1992 | Kurihara et al. |
| 5,122,418 | A | 6/1992 | Nakane et al. |
| 5,133,803 | A | 7/1992 | Moffatt |
| 5,145,518 | A | 9/1992 | Winnik et al. |
| 5,145,727 | A | 9/1992 | Potts et al. |
| 5,169,706 | A | 12/1992 | Collier, IV et al. |
| 5,174,959 | A | 12/1992 | Kundu et al. |
| 5,178,931 | A | 1/1993 | Perkins et al. |
| 5,183,656 | A | 2/1993 | Uesaka et al. |
| 5,188,885 | A | 2/1993 | Timmons et al. |
| 5,196,177 | A | 3/1993 | Watanabe et al. |
| 5,204,429 | A | 4/1993 | Kaminsky et al. |
| 5,209,998 | A | 5/1993 | Kavassalis et al. |
| 5,220,000 | A | 6/1993 | Theodoropulos |
| 5,221,497 | A | 6/1993 | Watanabe et al. |
| 5,225,374 | A | 7/1993 | Fare et al. |
| 5,230,953 | A | 7/1993 | Tsugeno et al. |
| 5,238,518 | A | 8/1993 | Okubi et al. |
| 5,245,117 | A * | 9/1993 | Withers et al. ................ 588/249 |
| 5,266,289 | A | 11/1993 | Tsugeno et al. |
| 5,284,703 | A | 2/1994 | Everhart et al. |
| 5,286,624 | A | 2/1994 | Terashima et al. |
| 5,292,868 | A | 3/1994 | Subramanian |
| 5,294,717 | A | 3/1994 | Theodoropulos |
| 5,300,365 | A | 4/1994 | Ogale |
| 5,322,061 | A | 6/1994 | Brunson |
| 5,332,432 | A | 7/1994 | Okubi et al. |
| 5,338,713 | A | 8/1994 | Takagi et al. |
| 5,342,876 | A | 8/1994 | Abe et al. |
| 5,350,624 | A | 9/1994 | Georger et al. |
| 5,366,947 | A | 11/1994 | Müller et al. |
| 5,382,400 | A | 1/1995 | Pike et al. |
| 5,383,450 | A | 1/1995 | Hubbard et al. |
| 5,389,338 | A * | 2/1995 | Fish ........................... 422/401 |
| 5,397,667 | A | 3/1995 | Law et al. |
| 5,407,442 | A | 4/1995 | Karapasha |
| 5,407,600 | A | 4/1995 | Ando et al. |
| 5,420,016 | A | 5/1995 | Boguslaski et al. |
| 5,420,090 | A | 5/1995 | Spencer et al. |
| 5,427,844 | A | 6/1995 | Murai et al. |
| 5,429,628 | A | 7/1995 | Trinh et al. |
| 5,432,094 | A | 7/1995 | Delente |
| 5,451,450 | A | 9/1995 | Erderly et al. |
| 5,458,864 | A | 10/1995 | Tsugeno et al. |
| 5,467,778 | A | 11/1995 | Catt et al. |
| 5,472,775 | A | 12/1995 | Obijeski et al. |
| 5,480,636 | A | 1/1996 | Maruo et al. |
| 5,486,356 | A | 1/1996 | Yim |
| 5,487,938 | A | 1/1996 | Spencer et al. |
| 5,488,126 | A | 1/1996 | Subramanian et al. |
| 5,527,171 | A | 6/1996 | Soerensen |
| 5,538,548 | A | 7/1996 | Yamazaki |
| 5,539,124 | A | 7/1996 | Etherton et al. |
| 5,540,916 | A | 7/1996 | Parks |
| 5,547,607 | A | 8/1996 | Ando et al. |
| 5,553,608 | A | 9/1996 | Reese et al. |
| 5,554,775 | A | 9/1996 | Krishnamurti et al. |
| 5,580,655 | A | 12/1996 | El-Shall et al. |
| 5,583,219 | A | 12/1996 | Subramanian et al. |
| 5,591,797 | A | 1/1997 | Barthel et al. |
| 5,597,512 | A | 1/1997 | Watanabe et al. |
| 5,657,762 | A | 8/1997 | Coley et al. |
| 5,661,198 | A | 8/1997 | Inatani et al. |
| 5,663,224 | A | 9/1997 | Emmons et al. |
| 5,679,138 | A | 10/1997 | Bishop et al. |
| 5,679,724 | A | 10/1997 | Sacripante et al. |
| 5,695,868 | A | 12/1997 | McCormack |
| 5,733,272 | A | 3/1998 | Brunner et al. |
| 5,773,227 | A | 6/1998 | Kuhn et al. |
| 5,795,985 | A | 8/1998 | Hüsler et al. |
| 5,813,398 | A | 9/1998 | Baird et al. |
| 5,817,300 | A | 10/1998 | Cook et al. |
| 5,833,952 | A | 11/1998 | Grigor et al. |
| 5,837,352 | A | 11/1998 | English et al. |
| 5,843,509 | A | 12/1998 | Calvo Salve et al. |
| 5,855,788 | A | 1/1999 | Everhart et al. |
| 5,861,144 | A | 1/1999 | Peterson et al. |

(56) References Cited

U.S. PATENT DOCUMENTS

| | | | |
|---|---|---|---|
| 5,871,872 A | 2/1999 | Matijevic et al. | |
| 5,874,067 A | 2/1999 | Lucas et al. | |
| 5,880,176 A | 3/1999 | Kamoto et al. | |
| 5,880,309 A | 3/1999 | Suzuki et al. | |
| 5,882,638 A | 3/1999 | Dodd et al. | |
| 5,885,599 A | 3/1999 | Peterson et al. | |
| 5,897,541 A | 4/1999 | Uitenbroek et al. | |
| 5,902,226 A | 5/1999 | Tasaki et al. | |
| 5,905,101 A | 5/1999 | Fujiki et al. | |
| 5,916,596 A | 6/1999 | Desai et al. | |
| 5,948,398 A | 9/1999 | Hanamoto et al. | |
| 5,948,483 A | 9/1999 | Kim et al. | |
| 5,962,566 A | 10/1999 | Grandfils et al. | |
| 5,964,926 A | 10/1999 | Cohen | |
| 5,972,389 A | 10/1999 | Shell et al. | |
| 5,985,229 A | 11/1999 | Yamada et al. | |
| 5,989,510 A | 11/1999 | Abe et al. | |
| 5,989,515 A | 11/1999 | Watanabe et al. | |
| 5,989,840 A | 11/1999 | D'Angelo et al. | |
| 6,004,625 A | 12/1999 | Ohshima | |
| 6,007,592 A | 12/1999 | Kasai et al. | |
| 6,024,786 A | 2/2000 | Gore | |
| 6,039,923 A | 3/2000 | Klemm et al. | |
| 6,045,900 A | 4/2000 | Haffner et al. | |
| 6,047,413 A | 4/2000 | Welchel et al. | |
| 6,057,162 A | 5/2000 | Rounbehler et al. | |
| 6,060,410 A | 5/2000 | Gillberg-LaForce et al. | |
| 6,073,771 A | 6/2000 | Pressley et al. | |
| 6,075,179 A | 6/2000 | McCormack et al. | |
| 6,096,299 A | 8/2000 | Guarracino et al. | |
| 6,111,163 A | 8/2000 | McCormack et al. | |
| 6,123,676 A | 9/2000 | Anapliotis | |
| 6,171,811 B1 | 1/2001 | Becerro De Bengoa Vallejo | |
| 6,172,173 B1 | 1/2001 | Spencer et al. | |
| 6,177,608 B1 | 1/2001 | Weinstrauch | |
| 6,190,814 B1 | 2/2001 | Law et al. | |
| 6,193,844 B1 | 2/2001 | McLaughlin et al. | |
| 6,225,524 B1 | 5/2001 | Guarracino et al. | |
| 6,228,605 B1 | 5/2001 | Marshall | |
| 6,234,974 B1 | 5/2001 | Catt et al. | |
| 6,238,767 B1 | 5/2001 | McCormack et al. | |
| 6,254,894 B1 | 7/2001 | Denkewicz, Jr. et al. | |
| 6,264,615 B1 | 7/2001 | Diamond et al. | |
| 6,277,346 B1 | 8/2001 | Murasawa et al. | |
| 6,277,772 B1 | 8/2001 | Gancet et al. | |
| 6,291,535 B1 | 9/2001 | Watanabe et al. | |
| 6,294,222 B1 | 9/2001 | Cohen et al. | |
| 6,299,867 B1 | 10/2001 | Aoyagi et al. | |
| 6,309,736 B1 | 10/2001 | McCormack et al. | |
| 6,312,918 B1 | 11/2001 | Ito et al. | |
| 6,315,864 B2 | 11/2001 | Anderson et al. | |
| 6,334,988 B1 | 1/2002 | Gallis et al. | |
| 6,344,218 B1 | 2/2002 | Dodd et al. | |
| 6,344,272 B1 | 2/2002 | Oldenburg et al. | |
| 6,358,537 B1 | 3/2002 | Hoshino et al. | |
| 6,358,909 B1 | 3/2002 | Ochomogo et al. | |
| 6,369,290 B1 | 4/2002 | Glaug et al. | |
| 6,376,741 B1 | 4/2002 | Guarracino et al. | |
| 6,387,495 B1 | 5/2002 | Reeves et al. | |
| 6,391,262 B1 | 5/2002 | Brinton et al. | |
| 6,398,827 B1 | 6/2002 | Ota et al. | |
| 6,403,380 B1 | 6/2002 | Catt et al. | |
| 6,406,669 B1 | 6/2002 | Duan et al. | |
| 6,410,765 B1 | 6/2002 | Wellinghoff et al. | |
| 6,425,530 B1 | 7/2002 | Coakley | |
| 6,427,693 B1 | 8/2002 | Blackstock et al. | |
| 6,428,814 B1 | 8/2002 | Bosch et al. | |
| 6,433,243 B1 | 8/2002 | Woltman et al. | |
| 6,440,187 B1 | 8/2002 | Kasai et al. | |
| 6,451,619 B1 | 9/2002 | Catt et al. | |
| 6,454,726 B1 | 9/2002 | Catt et al. | |
| 6,460,989 B1 | 10/2002 | Yano et al. | |
| 6,461,735 B1 | 10/2002 | Furuya et al. | |
| 6,467,897 B1 | 10/2002 | Wu et al. | |
| 6,468,500 B1 | 10/2002 | Sakaguchi et al. | |
| 6,475,601 B1 | 11/2002 | Sakaki et al. | |
| 6,479,150 B1 | 11/2002 | Liu et al. | |
| 6,479,278 B2 | 11/2002 | Marshall | |
| 6,491,790 B1 | 12/2002 | Proverb et al. | |
| 6,498,000 B2 | 12/2002 | Murasawa et al. | |
| 6,509,169 B2 | 1/2003 | Ratcliff et al. | |
| 6,517,199 B1 | 2/2003 | Tomioka et al. | |
| 6,531,704 B2 | 3/2003 | Yadav et al. | |
| 6,533,826 B1 | 3/2003 | Gessner et al. | |
| 6,536,890 B1 | 3/2003 | Kato et al. | |
| 6,544,492 B1 | 4/2003 | DeBerry | |
| 6,548,264 B1 | 4/2003 | Tan et al. | |
| 6,551,457 B2 | 4/2003 | Westman et al. | |
| 6,562,441 B1 | 5/2003 | Maeda et al. | |
| 6,575,383 B2 | 6/2003 | Dobler et al. | |
| 6,578,521 B2 | 6/2003 | Raymond et al. | |
| 6,585,663 B1 | 7/2003 | Coley et al. | |
| 6,589,562 B1 | 7/2003 | Shefer et al. | |
| 6,589,761 B1 | 7/2003 | Freadman et al. | |
| 6,607,711 B2 * | 8/2003 | Pedersen | 424/49 |
| 6,617,488 B1 | 9/2003 | Springer et al. | |
| 6,623,848 B2 | 9/2003 | Brehm et al. | |
| 6,627,377 B1 | 9/2003 | Itatani et al. | |
| 6,638,918 B2 | 10/2003 | Davison et al. | |
| 6,639,004 B2 | 10/2003 | Falat et al. | |
| 6,645,569 B2 | 11/2003 | Cramer et al. | |
| 6,693,071 B2 | 2/2004 | Ghosh et al. | |
| 6,706,537 B2 | 3/2004 | Ignacio et al. | |
| 6,818,194 B2 | 11/2004 | DeBerry et al. | |
| 6,821,786 B2 | 11/2004 | Rupp | |
| 6,825,040 B2 | 11/2004 | Scaringe et al. | |
| 6,927,064 B1 | 8/2005 | Catt et al. | |
| 7,014,612 B2 | 3/2006 | Hubbard et al. | |
| 7,022,285 B2 | 4/2006 | Arai et al. | |
| 7,052,854 B2 | 5/2006 | Melker et al. | |
| 7,101,340 B1 | 9/2006 | Braun | |
| 7,141,518 B2 | 11/2006 | MacDonald et al. | |
| 2001/0000889 A1 | 5/2001 | Yadav et al. | |
| 2001/0023338 A1 | 9/2001 | Guarracino et al. | |
| 2001/0031248 A1 | 10/2001 | Hall-Puzio et al. | |
| 2001/0056246 A1 | 12/2001 | Rodriguez-Fernandez | |
| 2002/0005145 A1 | 1/2002 | Sherman | |
| 2002/0066542 A1 | 6/2002 | Jakob et al. | |
| 2002/0091071 A1 | 7/2002 | Fischer et al. | |
| 2002/0106466 A1 | 8/2002 | Hausmann et al. | |
| 2002/0110686 A1 | 8/2002 | Dugan | |
| 2002/0111561 A1 | 8/2002 | Kaga et al. | |
| 2002/0128336 A1 | 9/2002 | Kolb et al. | |
| 2002/0142937 A1 | 10/2002 | Carter et al. | |
| 2002/0149656 A1 | 10/2002 | Nohr et al. | |
| 2002/0150678 A1 | 10/2002 | Cramer et al. | |
| 2002/0176982 A1 | 11/2002 | Rohrbaugh et al. | |
| 2002/0177621 A1 | 11/2002 | Hanada | |
| 2002/0182102 A1 | 12/2002 | Fontenot et al. | |
| 2002/0182658 A1 | 12/2002 | Polak et al. | |
| 2003/0003589 A1 | 1/2003 | Khalil et al. | |
| 2003/0013369 A1 | 1/2003 | Soane et al. | |
| 2003/0021983 A1 | 1/2003 | Nohr et al. | |
| 2003/0050211 A1 | 3/2003 | Hage et al. | |
| 2003/0056648 A1 | 3/2003 | Fornai et al. | |
| 2003/0070782 A1 | 4/2003 | Proverb et al. | |
| 2003/0082237 A1 * | 5/2003 | Cha et al. | 424/490 |
| 2003/0100842 A1 | 5/2003 | Rosenberg et al. | |
| 2003/0130631 A1 | 7/2003 | Springer et al. | |
| 2003/0147956 A1 | 8/2003 | Shefer et al. | |
| 2003/0147966 A1 | 8/2003 | Franzen et al. | |
| 2003/0181540 A1 | 9/2003 | Quellet et al. | |
| 2003/0203009 A1 | 10/2003 | MacDonald | |
| 2003/0211618 A1 | 11/2003 | Patel | |
| 2003/0216660 A1 | 11/2003 | Ben-Oren et al. | |
| 2003/0235605 A1 | 12/2003 | Lelah et al. | |
| 2004/0029171 A1 | 2/2004 | Wagner et al. | |
| 2004/0033269 A1 | 2/2004 | Hei et al. | |
| 2004/0034157 A1 | 2/2004 | Ghosh et al. | |
| 2004/0043688 A1 | 3/2004 | Soerens et al. | |
| 2004/0077093 A1 | 4/2004 | Pan | |
| 2004/0120904 A1 | 6/2004 | Lye et al. | |
| 2004/0120921 A1 | 6/2004 | Quincy, III et al. | |
| 2004/0122387 A1 | 6/2004 | Long et al. | |

(56) References Cited

U.S. PATENT DOCUMENTS

| | | |
|---|---|---|
| 2004/0142041 A1 | 7/2004 | MacDonald et al. |
| 2004/0175556 A1 | 9/2004 | Clark et al. |
| 2004/0235183 A1 | 11/2004 | Coley et al. |
| 2005/0012085 A1 | 1/2005 | Lavi et al. |
| 2005/0084412 A1 | 4/2005 | MacDonald et al. |
| 2005/0084438 A1 | 4/2005 | Do et al. |
| 2005/0084464 A1 | 4/2005 | McGrath et al. |
| 2005/0084474 A1 | 4/2005 | Wu et al. |
| 2005/0084632 A1 | 4/2005 | Urlaub et al. |
| 2005/0084977 A1 | 4/2005 | Boga et al. |
| 2005/0112085 A1 | 5/2005 | MacDonald et al. |
| 2005/0113771 A1 | 5/2005 | MacDonald et al. |
| 2005/0124072 A1 | 6/2005 | Boga et al. |
| 2005/0130311 A1 | 6/2005 | Coley et al. |
| 2005/0131363 A1 | 6/2005 | MacDonald et al. |
| 2005/0164320 A1 | 7/2005 | McDevitt et al. |
| 2005/0171454 A1 | 8/2005 | Catt et al. |
| 2005/0186109 A1 | 8/2005 | Nakamura et al. |
| 2005/0191704 A1 | 9/2005 | Boga et al. |
| 2005/0196812 A1 | 9/2005 | Williams |
| 2006/0003336 A1 | 1/2006 | Song et al. |

FOREIGN PATENT DOCUMENTS

| | | |
|---|---|---|
| EP | 0251783 A2 | 1/1988 |
| EP | 0282287 B2 | 9/1988 |
| EP | 0339461 B1 | 11/1989 |
| EP | 034897 A2 | 1/1990 |
| EP | 0376448 B1 | 7/1990 |
| EP | 0389015 A2 | 9/1990 |
| EP | 0389023 A2 | 9/1990 |
| EP | 0389023 A3 | 9/1990 |
| EP | 0483500 A1 | 5/1992 |
| EP | 0510619 A1 | 10/1992 |
| EP | 0749295 B1 | 12/1996 |
| EP | 0972563 A1 | 1/2000 |
| EP | 10134800 A1 | 9/2000 |
| EP | 1053788 A1 | 11/2000 |
| EP | 1157672 A1 | 11/2001 |
| EP | 1162172 A1 | 12/2001 |
| EP | 1188854 A1 | 3/2002 |
| EP | 1214878 A1 | 6/2002 |
| EP | 1216675 A1 | 6/2002 |
| EP | 1298071 A1 | 4/2003 |
| EP | 1315526 B1 | 6/2003 |
| JP | 62149322 | 7/1987 |
| JP | 3221142 | 9/1991 |
| WO | WO8902698 A1 | 4/1989 |
| WO | WO9111977 A1 | 8/1991 |
| WO | WO9112029 A1 | 8/1991 |
| WO | WO9112030 A1 | 8/1991 |
| WO | WO9619346 A2 | 6/1996 |
| WO | WO9619346 A3 | 6/1996 |
| WO | WO9705482 A1 | 2/1997 |
| WO | WO9725076 A1 | 7/1997 |
| WO | WO9820915 A1 | 5/1998 |
| WO | WO9826808 A2 | 6/1998 |
| WO | WO9826808 A3 | 6/1998 |
| WO | WO9947252 A3 | 9/1999 |
| WO | WO0003797 A1 | 1/2000 |
| WO | WO0029036 A2 | 3/2000 |
| WO | WO0029036 A3 | 3/2000 |
| WO | WO00137764 A1 | 3/2000 |
| WO | WO0059555 A1 | 10/2000 |
| WO | WO0076558 A1 | 12/2000 |
| WO | WO0106054 A1 | 1/2001 |
| WO | WO0226272 A1 | 4/2002 |
| WO | WO0249559 A2 | 6/2002 |
| WO | WO02055115 A1 | 7/2002 |
| WO | WO02062881 A2 | 8/2002 |
| WO | WO02064877 A2 | 8/2002 |
| WO | WO02083297 A1 | 10/2002 |
| WO | WO02084017 A1 | 10/2002 |
| WO | WO02094329 A1 | 11/2002 |
| WO | WO02095112 A1 | 11/2002 |
| WO | WO03000979 A2 | 1/2003 |
| WO | WO03025067 A1 | 3/2003 |
| WO | WO03032959 A1 | 4/2003 |
| WO | WO03088931 A2 | 10/2003 |
| WO | WO03092885 A1 | 11/2003 |
| WO | WO04000986 A1 | 12/2003 |

OTHER PUBLICATIONS

Abstract of Japanese Patent No. JP05098185 Apr. 20, 1993.
Abstract of Japanese Patent No. JP1262868 Oct. 19, 1989.
Abstract of Japanese Patent No. JP198610366 Jan. 11, 1986.
Abstract of Japanese Patent No. JP2001208753 Mar. 8, 2001.
Abstract of Japanese Patent No. JP2157039 Jun. 15, 1990.
Abstract of Japanese Patent No. JP3195562 Aug. 27, 1991.
Abstract of Japanese Patent No. JP4335141 Nov. 24, 1992.
Abstract of Japanese Patent No. JP5106199 Apr. 27, 1993.
Abstract of Japanese Patent No. JP5261246 Oct. 12, 1993.
Abstract of Japanese Patent No. JP57135360 Aug. 20, 1982.
Abstract of Japanese Patent No. JP6285140 Oct. 11, 1994.
Abstract of Japanese Patent No. JP63072337 Apr. 2, 1988.
Abstract of Japanese Patent No. JP7256025 Oct. 9, 1995.
Abstract of Japanese Patent No. JP8152409 Jun. 11, 1996.
Abstract of Japanese Patent No. JP9143872 Jun. 3, 1997.
Abstract of Japanese Patent No. JP92067913 Oct. 29, 1992.
Abstract of SU834073 May 30, 1981.
Abstract of Article—*Non-hydrothermal synthesis of copper-, zinc- and copper-zinc hydrosilicates*, T. M. Yurieva et al., Materials Research Innovations, vol. 5, No. 1, Jun. 2001, pp. 3-11.
Article—*A new method for predicting and confirming ovulation*, Albrecht, B.H. et al., (1985), Fertility and Sterility, 44(2), 200-5.
Article—*A Relationship Between Human Oral Bacteria and the Menstrual Cycle*, Prout, R.E., et al, (1970), The Journal of Periodontology, pp. 30-33.
Article—*A sorbent tube for oral malodour monitoring*, Julia Rodríguez-Fernández et al., Talanta, vol. 62, 2004, pp. 421-426.
Article—*Adsorption of Dyes on Nanosize Modified Silica Particles*, Guangwei Wu et al., Journal of Colloid and Interface Sciences, vol. 195, 1997, pp. 222-228.
Article—*Adsorption of Gases in Multimolecular Layers*, Stephen Brunauer et al., The Journal of the American Chemical Society, vol. 60, Feb. 1938, pp. 309-319.
Article—*Adsorption of Proteins and Antibiotics on Porous Alumina Membranes*, Yi Hua Ma et al., Fundamentals of Adsorption, vol. 80, 1992, pp. 389-396.
Article—*Ammonia vapour in the mouth as a diagnostic marker for Helicobacter pylori infection: preliminary "proof of principle" pharmacological investigations*, C. D. R. Dunn et al., British Journal of Biomedical Science, vol. 58, 2001, pp. 66-76.
Article—*Applicability of a SPME method for the Rapid Determination of VOCs*, Bénéet al., Chimia, vol. 56, No. 6, 2002, pp. 289-291.
Article—*Breath biomarkers for detection of human liver diseases, preliminary study*, Sehnert, S.S. et al., (2002), Biomarkers, 7, 174-187.
Article—*Breath pentane analysis as an index of lipid peroxidation, a functional test of vitamin E status*, Lemoyne, M. et al., (1987), American Journal of Clinical Nutrition, 46, 267-272.
Article—*Changes in Concentration of Volatile Sulfur Compounds of Mouth Air during the Menstrual Cycle*, Tonzetich, J. et al., (1978A), Journal of International Medical Research, 6, 245-254.
Article—*Characterisation of novel modified active carbons and marine algal biomass for the selective adsorption of lead*, Malik et al., Water Research, vol. 36, 2002, pp. 1527-1538.
Article—*Comparison of non-invasive tests to detect helicobacter pylori infection in children and adolescents, results of a multicenter European study*, Megraud, F. et al., (2005), Journal of Pediatrics, 146, 198-203.
Article—*Development of novel dye-doped silica nanoparticles for biomarker application*, Swadeshmukul Santra et al., Journal of Biomedical Optics, vol. 6, No. 2, Apr. 2001, pp. 160-166.
Article—*E-nose technologies promise new diagnostic instruments*, Skelley, D.S., (2000), IVD Technology, Jan.-Feb. issue.

(56) References Cited

OTHER PUBLICATIONS

Article—*Exhaled nitric oxide, the missing link between asthma and obesity*, de Winder-de Groot et al., (2005), Journal of Allergy and Clinical Immunology, 115, 419-420.

Article—*Fe-MCM-41 for Selective Epoxidation of Styrene with Hydrogen Peroxide*, Qinghong Zhang et al., The Chemical Society of Japan, Chemistry Letters 2001, pp. 946-947.

Article—*From Cyclodextrin Assemblies to Porous Materials by Silica Templating*, Sebastian Polarz et al., Angew. Chem. Int., vol. 40, No. 23, 2001, pp. 4417-4421.

Article—*Grafting of Poly (ethylenimine) onto Mesylated Cellulose Acetate, Poly (methyl methacrylate) and Poly(vinyl chloride)*, Christopher J. Biermann et al., Carbohydrate Polymers, vol. 12, 1990, pp. 323-327.

Article—*Immobilization of $(n-Bu_{4N})_4W_{10}O_{32}$ on Mesoporous MCM-41 and Amorphous Silicas for Photocatalytic Oxidation of Cycloalkanes with Molecular Oxygen*, Andrea Maldotti et al., Journal of Catalysis, vol. 209, 2002, pp. 210-216.

Article—*Immunization of mice with peptomers covalently couopled to aluminum oxide nanoparticles*, Andreas Frey et al., Vaccine, vol. 17, 1999, pp. 3007-3019.

Article—*Increase in exhaled carbon dioxide during exacerbations of cystic fibrosis*, Antuni, J.D. et al., (2000), Thorax, 55, 138-142.

Article—*Increase of acetone and ammonia in urine headspace and breath during ovulation quantified using selected ion tube mass spectrometry*, Diskin, A.M. et al., (2003), Physiological Measurement, 24, 191-199.

Article—*Increased carbon monoxide in exhaled air of asthmatic patients*, Zayasu, K. et al., (1997), Journal of Respiratory Critical Care Medicine, 156, 1140-1143.

Article—*Increased carbon monoxide in exhaled air of subjects with upper respiratory tract infections* Yamaya, M. et al., (1998), Journal of Respiratory Critical Care Medicine, 158, 311-314.

Article—*Increased levels of exhaled carbon monoxide in bronchiectasis, a new marker of oxidative stress*, Horvath, I., et al, (1998), Thorax, 53, 867-870.

Article—*Ion-trap detection of volatile organic compounds in alveolar breath*, Philips, M. et al., (1992), Clinical Chemistry, 38, 60-65.

Article—*Mesoporous Sieves with Unified Hybrid Inorganic/Organic Frameworks*, Brian J. Melde et al., Chem. Mater., vol. 11, No. 11, 1999, pp. 3302-3308.

Article—*Nanoparticles based on polyelectrolyte complexes: effect of structure and net charge on the sorption capability for solved organic molecules*, H.-M. Buchhammer et al., Colloid Polym. Sci., vol. 278, 2000, pp. 841-847.

Article—*On-Line Detection of Volatile Compounds in Human Breath*, Bischoff, et al., (2000), 4th European Congress of Oto-Rhino Laryngology, head and neck surgery, pp. 1369-1375.

Article—*Optical fibre sensor for hydrogen sulphide monitoring in mouth air*, Julio Rodríguez-Fernández et al., Analytica Chimica Acta, vol. 471, 2002, pp. 13-23.

Article—*Oral malodour: an indicator of health status and oral cleanliness*, Tonzetich, J., (1978B), International Dental Journal, 28, 309-19.

Article—*Ovulation prediction from cyclic changes in salivary electrical conductivity*, Loweit, K. et al., (1990), American Journal of Obstetrics and Gynecology, 163(2), 708-710.

Article—*Pitfalls in the use of breath pentane measurements to assess lipid peroxidation*, Springfield, J.R. et al., (1994), Journal of Lipid Research, 35, 1497-1504.

Article—*Purification and Characterization of Urease from Helicobacter pylori*, Bruce E. Dunn et al., The Journal of Biological Chemistry, vol. 265, No. 16, Jun. 5, 1990, pp. 9464-1990.

Article—*Relationship between stressful situations, salivary flow rate and oral volatile sulfur-containing compounds*; Queiroz, C.S. et al., (2002), European Journal of Oral Sciences, 110, 337-340.

Article—*Sanguinaria extract, a new agent for the control of volatile sulfur compounds in the oral cavity*, Boulware, et al., Journal of the Society of Cosmetic Chemists, 1985, vol. 36, No. 4, pp. 297-302.

Article—*Saponins and Sapogenins. VIII. Surface Films of Echinocystic Acid and Derivatives*, C. R. Noller, J. Am. Chem. Soc., vol. 60, 1938, 3 pages.

Article—*Shaping exhale durations for breath CO detection for men with mild mental retardation*, Rea, J. et al., (2002), Journal of Applied Behavior Analysis, 35, 415-418.

Article—*Significance of Ammonia in the Genesis of Gastric Epithelial Lesions Induced by Helicobacter pylori: An in vitro Study with Different Bacterial Strains and Urea Concentrations*, P. Sommi et al., Digestion, vol. 57, 1996, pp. 299-304.

Article—*Significance of ammonia produced by Helicobacter pylori*, Shigeji Ito et al., European Journal of Gastroenterology & Hepatology, vol. 6, No. 2, 1994, pp. 167-174.

Article—*Sniffing Sinusitis*, Felton, M.J., (2004), Today's Chemist At Work, Jun. 2004 (http://www.tcawonline.org).

Article—*Spectrophotometric Assay of Thiols*, Peter C. Jocelyn, Methods in Enzymology, vol. 142, 1987, pp. 44-67.

Article—*Standard Practice for Obtaining Spectrometric Data for Object-Color Evaluation*, Published by *ASTM International*, Designation: E 1164-02.

Article—*Structure and properties of silica nanoclusters at high temperatures*, I. V. Schweigert et al., The American Physical Society, Physical Review B, vol. 65. No. 235410, pp. 1-9.

Article—*Study of the urea thermal decomposition (pyrolysis) reaction and importance to cyanuric acid production*, Peter M. Schaber et al., American Laboratory, Aug. 1999, pp. 13-21.

Article—*Synthesis of porous Silica with help from cyclodextrin aggregates*, Markus Antonietti, Max-Planck-Institut für Kolloid-und, Germany, 1 page.

Article—*The Colloid Chemistry of Silica*, American Chemical Society 200th National Meeting, Aug. 26-31, 1990, pp. 22-23 and pp. 52-59.

Article—*Validation of $^{13}C$-Urea Breath Test for the Diagnosis of Helicobacter Pylori Infection in the Singapore Population*, T. S. Chua et al., Singapore Medical Journal, vol. 43, No. 8, 2002, pp. 408-411.

Paper—*Uniform Deposition of Ultrathin Polymer Films on the Surfaces of $Al_2O_3$ Nanoparticles by a Plasma Treatment*, Donglu Shi et al., University of Cincinnati and University of Michigan, Jun. 2000, pp. 1-15.

Pocket Guide to Digital Printing, Frank Cost, Delmar Publishers, Albany, NY, ISBN 0-8273-7592-1, pp. 144-145.

Product Information Sheet for Snowtex®, 6 pages.

Search Report and Written Opinion for PCT/US2004/027626 dated Jul. 13, 2005, 17 pages.

\* cited by examiner

VISUAL INDICATING DEVICE FOR BAD BREATH

RELATED APPLICATIONS

The present application is a continuation of U.S. application Ser. No. 12/134,547, filed on Jun. 6, 2008, which is a continuation of U.S. application Ser. No. 10/687,270, filed on Oct. 16, 2003, which are incorporated herein in their its entirety by reference thereto.

BACKGROUND OF THE INVENTION

In the literature, bad breath is usually referred to as halitosis or oral odor. The term halitosis comes from the Latin Halitus, meaning breath and the Greek -osis, meaning abnormal condition. On one hand most people are not aware of their own breath (whether sweet or bad), while on the other hand most people usually feel too uncomfortable to inform a person that they have bad breath.

The breath freshening and oral hygiene areas are large markets which are continuing to grow. For example, market research has shown that consumers in the USA spent US$1.8 billion on toothpaste in 2000, around US$715 million on oral care gums, almost US$740 million on mouthwash and other dental rinses, and almost US$950 million on toothbrushes and dental floss. Although many of those products are primarily for the maintenance of oral health, consumers also buy them to ensure that their breath is pleasant. The US$625 million spent on breath fresheners other than gums and mouthwash, for example breath mints, is directly for this purpose.

The mouth and nasal passages are home to hundreds of bacterial species with various nutritional preferences. In otherwise healthy people, the very back of the tongue, rather than the teeth and gums, is the main source of bad breath. This region is poorly cleansed by saliva and contains numerous tiny invaginations in which bacteria can hide. These bacteria putrefy postnasal drip and other oral debris that can collect there. These tiny organisms thrive on proteins, and the chemical compounds that result from the digestion of these proteins include some fetid compounds. At any given time, oral bacteria may be producing hydrogen sulfide (rotten egg smell), methyl mercaptan and skatole (also present in feces); indole; cadaverine (associated with rotting corpses); putrescine (found in decaying meat); and isovaleric acid (the smell of sweaty feet).

Additional oral sources of bad breath include poor oral hygiene (especially if proteinaceous particles are left between teeth), gum inflammation, faulty dental work, unclean dentures and abscesses. Because a steady flow of saliva washes away bacteria and its resultant odorous chemical products, anything that promotes dryness (for example, breathing through one's mouth, fasting, prolonged talking, stress and many medications) can exacerbate the situation.

Some bad breath seems to be associated with actual periodontal disease and is therefore a useful clue to physicians and dentists. The presence of several key bacteria such as *Treponema Denticola*, *Porphyromonas Gingivalis* and *Bactericides Forsythesis* can be founding plaque or the tongue.

The chemical composition and concentrations of the odorous compounds associated with bad breath have been studied and reported in the literature (Krotoszynski et al, 1977; Tonzetich, 1971). The most common odorous compound in levels above the human detection threshold is hydrogen sulfide (>250 ppb), followed by other sulfur containing compounds such as methyl mercaptan and dimethylsulfide. The human nose can detect hydrogen sulfide levels as low as 0.02 ppm (v/v), and levels of 0.025 ppm and greater are deemed to be characteristic of bad breath in a person.

While there are numerous products and technologies that cure or treat bad breath, there are surprisingly few devices available on the market to help identify and alert a user to bad breath.

One clinical instrument which is currently used to measure ppm levels in patients' breath is the Halimeter™ breath tester (available from Interscan Corporation, Chatsworth, Calif.), which costs US$1200 and is not portable. Another device is the BreathAlert™ breath tester (available from Tanita Corporation, Arlington Heights, Ill.). This is a small hand-held unit which costs about US$25. It uses a heated wire to detect sulfide compounds in a person's breath and gives a read-out in four levels.

The Halimeter™ breath tester has high sensitivity for hydrogen sulfide but low sensitivity for methyl mercaptan, which is a significant contributor to halitosis caused by periodontal disease. The BreathAlert T™ breath tester unit was sensitive to sulfide concentration, but gave different numbers depending on the position of the meter from the mouth and how the user breathed or blew into the unit's intake area.

There are also other devices which use oral bacteria measurements to indicate bad breath (for example, a device available from Soft Lines International), but these are very expensive and take time to provide an indication of bad breath, and are therefore not particularly useful to a user who wants to conduct a "spot check" on their breath.

It would be very useful if users were able to check their breath before meetings or dates, while at the office or after a meal.

There is therefore a clear need for an affordable, portable and rapid indicator for testing for bad breath.

SUMMARY OF THE INVENTION

As used herein the terms "odorous compound" and "odor" refer to any molecule or compound detectable to the olfactory system. The term "bad breath" refers to unpleasant odors which are present in a person's breath in levels which are detectable by another person. The term "visual indicating agent" refers to a substance, a composition or a material that gives a visual indication when a bad breath odor is present in a person's breath in a sufficient concentration.

Visual indicating agents that are sensitive to very low levels (>10 parts per billion (ppb)) of sulfur and/or amine containing odors were identified. On exposure to low levels of these odors the color indicating agents change color, thereby indicating the presence of bad breath to the user.

Suitable visual indicating agents are 4,4'-bis(dimethylamino)-benzhydrol (BDMD or Michler's hydrol (MH)) and related dyes having the general formula (I) or (II).

Michler's hydrol was identified and demonstrated to be sensitive to very low levels (~20 ppb) of sulfur and/or amine volatile compounds, the major odorous components of bad breath. This dye was tested for its sensitivity to the various odors in bad breath (sulfurs and amines in particular, including bad breath caused by fish, garlic, onions and the like), and was determined to be a good visual indicating agent for bad breath detection.

Simple breath testing devices which contain at least one of the indicating agents were also developed, wherein the indicating agent changes color when a user has bad breath. The visual indicating agent is color sensitive to at least one odor present in bad breath.

The device includes a simple carrier portion defining a passage, such as a substantially transparent tube or straw, containing the visual indicating agent and which is open on at feast one end. While the invention will be described hereinafter with particular reference to straws and tubes, it will be understood that the invention is useful with various other shapes as well. For example, the shape of the passageway may be cylindrical, triangular, square, almond-shaped and so forth.

The visual indicating agent may be in the form of a powder, in solution, or may be coated onto a substrate, such as cellulose tissue or paper, a non-woven polypropylene/polyethylene substrate, a woven substrate, glass fibre, cotton, silk, rayon and so forth. The straw may be substantially flattened to allow for easier storage, while still permitting a patient to blow through the passage in the tube. The device may include a zone with at least one reference color to allow the user to compare the color of the indicating agent after exposure to his or her breath with the reference color, and so easily determine if there has been a color change.

In one embodiment, the device includes a conveniently sized and discreet plastic tube, such as a clear drinking straw containing the color indicating agent. The color indicating agent can be applied to a strip which is inserted into the straw or over an end of the straw, can be used in powder form or can be incorporated into a solution inside the straw.

In order to test his or her breath, the user breathes or blows into or onto the device, and a change in color of the indicating agent (which may be the fading of color, the development of color or a change from one color to another) indicates that the user has bad breath. This breath testing device therefore alerts the user of his or her bad breath and allows them to take appropriate action, such as to brush his or her teeth, use mouthwash or eat a breathmint.

A dispenser for containing and dispensing the breath testing devices was also developed, and in one embodiment, the dispenser with the breath testing devices is designed so that it can be sold together with, or later attached to a dispenser for at least one breath freshening agent, such as toothpaste, breath mints or the like.

DETAILED DESCRIPTION OF THE INVENTION

The invention provides simple visual breath testing devices which are able to detect levels of sulfur and/or ammonia compounds in a user's breath which are indicative of bad breath. Thus, the breath testing devices include a visual indicating agent that changes color in the presence of bad breath. The breath testing device is portable, discreet, disposable and relatively inexpensive to produce.

In one embodiment, the visual indicating agent is 4,4'-bis (dimethylamino)-benzhydrol, also known as "BDMD", "Michler's hydrol" or "MH". This indicating agent is sensitive to both sulfur-containing and ammonia-containing odors, changing from blue to colorless in the presence of these odors. Michler's Hydrol reacts with amine or sulfur compounds according to the following reaction:

Michler's Hydrol
(MH or BDMB)

-continued (Colorless)

In alternative embodiments, the visual indicating agent may be an indicating agent represented by the following general formula (I) or (II):

where,

| Indicating Agent | R | R' | R" | Indicating Agent for |
|---|---|---|---|---|
| Michler's Hydrol (MH) | $(CH_3)_2NC_6H_4-$ | $(CH_3)_2NC_6H_4-$ | H | Thiols, Mercaptans, Ammonia, Amines, Diamines and Polyamines |
| Pararosaniline (PAB) | $(NH_2)C_6H_4-$ | $(NH_2)C_6H_4-$ | $(NH_2)C_6H_4-$ | Ammonia, Amines, Diamines and Polyamines |
| Alpha-naphtholbenzein (ANB) | $C_6H_4-$ | (naphthol-OH) | (naphthoquinone =O) | Ammonia, Amines, Diamines and Polyamines |
| Naphthochrome Green (NCG) | $C_6H_4-$ | $NaO_2C$, OH naphthol | $CO_2Na$, naphthoquinone =O | Ammonia, Amines, Diamines and Polyamines |

The dye may change color by fading to a lighter color, by deepening in color or by actually changing from one color to another.

The degree of the color change will depend on the concentration of the indicating agent or the concentration of sulfur or ammonia compounds in the patient's breath. Therefore, in order to observe a color change in response to sulfur and/or ammonia levels >10 parts per billion (ppb), more preferably >20 ppb, and most preferably >25 ppb, the concentration of indicating agent which is used is preferably in the range of from 0.001 to 15% wt/wt, more preferably from 0.005 to 2% wt/wt, and most preferably from 0.1 to 0.5% wt/wt.

The substrate, typically a cellulose tissue, may be coated with nanoparticles to provide a high surface area coating on the substrate, i.e., higher than the cellulose fiber by itself. Thus, the cellulose tissue may be given a boost in surface area by coating it with the nanoparticles. The treated substrate may be then coated with the visual indicating dye. It's believed that this high surface area coating spreads the dye over the silica surface to provide a thinner coating and thus improving the sensitivity of the device.

The average size of the nanoparticles is generally less than about 100 nanometers, in fact it may be from about 1 to about 50 nanometers, and from about 4 to about 20 nanometers. As used herein, the average size of a particle refers to its average length, width, height, and/or diameter.

The nanoparticles may have a surface area of from about 50 square meters per gram ($m^2/g$) to about 1000 $m^2/g$, in some cases from about 100 $m^2/g$ to about 600 $m^2/g$, and in some cases, from about 180 $m^2/g$ to about 240 $m^2/g$.

In addition, the nanoparticles may also be relatively non-porous or solid. That is, the nanoparticles may have a pore volume that is less than about 0.5 milliliters per gram (ml/g), less than about 0.4 milliliters per gram, less than about 0.3 ml/g, and even from about 0.2 ml/g to about 0.3 ml/g. It is believed that the solid nature, i.e., low pore volume, of the nanoparticles may enhance the uniformity and stability of the nanoparticles.

Examples of commercially available alumina nanoparticles include, for instance, Aluminasol® 100, Aluminasol® 200 and Aluminasol® 520, which are available from Nissan Chemical America Corporation, Houston, Tex., USA. Alternatively, silica nanoparticles may be utilized, such as Snowtex-C®, Snowtex-O®, Snowtex-PS® and Snowtex-OXS® nanoparticles, which are also available from Nissan Chemical.

Snowtex-OXS® nanoparticles, for instance, have a particle size of from 4 to 6 nanometers, and may be ground into a powder having a surface area of approximately 509 square meters per gram. Also, alumina-coated silica particles may be used, such as Snowtex-AK® nanoparticles available from Nissan Chemical.

The breath testing device includes a simple supporting member, such as a substantially transparent tube or straw containing the visual indicating agent. The straw or tube may be substantially flattened to allow for easier storage, while still permitting a patient to blow through the passage in the tube.

The visual indicating agent may be in the form of a powder, in solution, or may be applied in solution onto a substrate, such as cellulose tissue or paper, cotton, a non-woven polypropylene/polyethylene substrate, a woven substrate, glass fiber, silk, rayon, fabric, fiber, spunbond, synthetic polymer and so forth, and dried, leaving a dried residue. The indicating agent may also be printed in solution onto the substrate, for example by using an inkjet printer. The term "in solution" as used herein refers to a liquid solution of the indication agent in water, an aqueous solution or solvent such as alcohol or toluene.

The breath testing device may include a zone with at least one reference color or shade of color to allow the user to compare the color of the indicating agent after exposure to his or her breath with the reference color, and so easily determine if there has been a color change.

In one embodiment, the visual indicating agent is coated onto a cellulose substrate which is then inserted into a straw. In another embodiment, the visual indicating agent is again coated onto a cellulose substrate, but is placed over one end of a straw.

In both embodiments, when a user blows into the tube, their breath will pass through the tube and over or through the substrate, thus causing the indicating agent to change color if levels of sulfur and/or ammonia compounds which are indicative of bad breath (generally >=25 ppb) are present in the user's breath.

According to another embodiment, the breath testing devices described above were made smaller in size so that several of the breath testing devices could be easily packaged together in a pocket-sized container. A straw was cut to about 4 cm in length, and a dye-treated substrate was either inserted into the straw or was placed over one end of the straw. The straw was then substantially flattened by laminating it in a standard business card heated laminator so that air was still able to pass through the tube of the straw.

A dispenser for containing and dispensing the breath testing devices was also developed, and in one embodiment, a pocket-sized dispenser for containing and dispensing several breath testing devices was designed so that it can be sold together with, or later attached to, a dispenser for a breath freshening agent, such as toothpaste, breath mints or the like.

Unless otherwise specified, chemicals and biochemicals were obtained from Sigma-Aldrich of Milwaukee, Wis. Absorbance readings were measured using a microplate reader from Dynex Technologies of Chantilly, Va. (Model 4 MRX).

The most widely used color test is called CIELAB and is discussed in *Pocket Guide to Digital Printing* by F. Cost, Delmar Publishers, Albany, N.Y. ISBN 0-8273-7592-1 at pages 144 and 145. This method defines three variables, $L^*$, $a^*$, and $b^*$, that correspond to three characteristics of perceived color based on the opponent theory of color perception. The three variables have the following meaning:

$L^*$=Lightness, ranging from 0 to 100. Where 0=dark and 100=light, $a^*$=Red/green axis, ranging approximately from −100 to 100. Positive values are reddish and negative values are greenish.

$b^*$=Yellow/blue axis, Ranging approximately from −100 to 100. Positive values are yellowish and negative values are blueish.

Because CIELAB color space is somewhat uniform, a single number can be calculated that represents the difference between two colors as perceived by a human being. This difference is termed $\Delta E$ and is calculated by taking the square root of the sum of the squares of the three differences ($\Delta L^*$, $\Delta a^*$, and $\Delta b^*$) between the two colors. In CIELAB color space, each $\Delta E$ unit is roughly a just-noticeable difference between two colors. So that the two colors have a difference of, for example, 4.4, the human eye can perceive the difference in color between the two colors. CIELAB is therefore a good measure for an objective device-independent color specification system that can be used as a reference color space for the purpose of color management and expression of changes in color.

Color intensities ($L^*a^*b^*$ values) herein were measured using a handheld spectrophotometer from Minolta Co. Ltd. of Osaka, Japan (Model #CM2600d). This instrument utilizes the D/8 geometry conforming to CIE No. 15, ISO 772411, ASTM E1164 and JIS Z8722-1982 (diffused illumination) 8 degree viewing system, The D65 light reflected by the specimen surface at an angle of 8 degrees to the normal of the surface is received by the specimen-measuring optical system.

An acetate buffer containing 40 mM sodium acetate and 4 M guanidine HCl, pH 5.1, was used for preparations of the indicating agents.

Paper towels or KIMWIPES® tissues from Kimberly-Clark Corporation of Dallas, Tex., USA were coated with Snowtex-O® nanoparticles (pH 4.1), available from Nissan Chemical, and were used in the examples described herein with Milchler's hydrol dye (MH or BDMB) where dye was added without acetate buffer, unless otherwise indicated.

The invention will now be described in more detail by way of the following non-limiting examples.

Example 1

1 ml of a reaction mixture was placed into each of 6 vials containing 10 µl of furfuryl mercaptan (0, 0.228, 0.456, 0.912, 1.824 and 3.648 ppm, respectively), 980 µl of buffer containing 40 mM sodium acetate and 4 M guanidine chloride, pH 5.1 and 10 µl of 0.65 mg/ml MH dye (BDMB). After incubation of all the vials at room temperature for less than 5 minutes, a 200 µl portion from each vial was transferred to a microtiter plate well, and the absorbances at 590 nm were measured using a microtiter plate reader. The absorbances can also be measured in the range of 580-615 nm.

Figure 1:
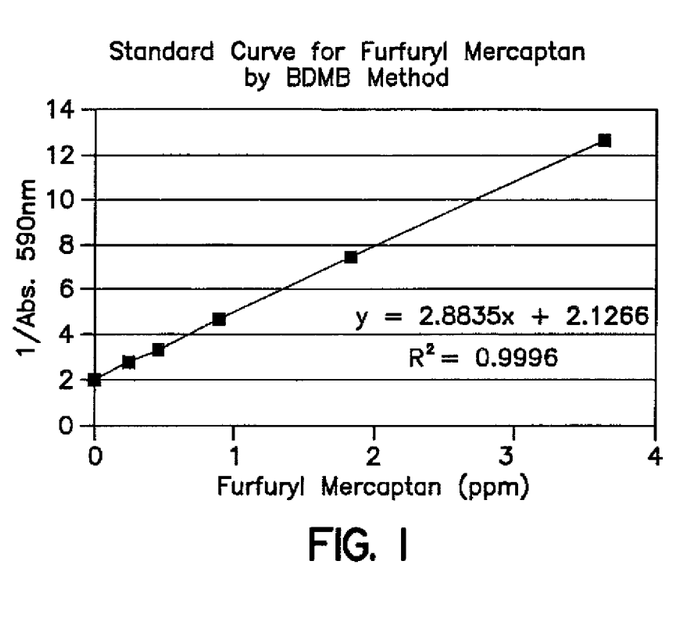
FIG. 1 shows a standard curve for the detection of furfuryl mercaptan by Michler's Hydrol-dye.

As shown in FIG. 1, a standard curve was derived using furfuryl mercaptan as a model thiol odorous compound detectable by MH dye. In FIG. 1 the x-axis is the concentration of furfuryl mercaptan in ppm from 0 to 4 and the y-axis is the inverse of the absorbance at 590 nm. The sensitivity of thiol detection was found to be very high in this method.

Example 2

As garlic is a common cause of bad breath, Michler's Hydrol (MH) was tested to see if it is a sensitive indicating agent for garlic odors. Garlic vapor has a sulfur compound (diallyl thiosulfinate (allicin)) as its major odorous component. Fresh-cut garlic was placed in a jar with a MH-dyed Scott® paper towel, and the jar was sealed. The paper towel in the garlic containing jar was observed to change color (from blue to colorless) within 3-5 minutes, whereas no color change was observed in a control jar.

Example 3

The experiment was repeated, but instead of using MH dye only, the MH dye was mixed with dyes which are not color sensitive to the odors present in bad breath, such as food dyes, in order to create alternative indicating colors. Exposure of the mixed dye to bad breath odors caused the MH-dye to become colorless, thus resulting in the area coated with the mixed dye to change from the mixed color to the food dye color (Table 1).

TABLE 1

Combinations Of MH-dye and non-odor sensitive dyes

| Dye | Color Before Odor | Color After Odor Exposure |
|---|---|---|
| Food Red No. 40 | Red | Red |
| Food Red 40/ Michler's Hydrol | Purple | Red |
| Food Yellow No. 5 | Yellow | Yellow |
| Food Yellow No.5/ Michler's Hydrol | Green | Yellow |

Example 4

As an alternative to coating a solution of the indicating agent onto a cellulose substrate as described in examples 1 to 3 above, a solution of the indicating agent was formulated into an inkjet printable ink. Inkjet printing deposits a thin coating of dye on top of the substrate, potentially allowing a more sensitive color coating on the substrate. The Michler's Hydrol dye solution was formulated with inkjet additives shown in Table 2 below.

TABLE 2

Inkjet formulation

| INK COMPONENT | VOLUME (ml) |
|---|---|
| Water (deionized) | 0.85 |
| Ethylene Glycol | 3.0 |
| Glycerol | 1.5 |
| Polyethylene Glycol (200 MW) | 3.0 |
| 1,3-Propanediol | 1.5 |
| Michler's Hydrol (1.5 mg/ml) in 40 mM sodium acetate and 4M guanidine HCl, pH 5.1 | 40.1 |
| TOTAL | 50 |

The ink solution was loaded into empty Margarita™ cartridges (part no. 0900400-300) obtained from McDermid-Colorspan of Eden Prairie, Minn. and printed using a wide format McDermid-Colorspan printer (Model XII). Good inkjet printing on Scott® paper towel substrate was demonstrated. A strip of the printed Scott® paper towel was then exposed to garlic odor and the blue color was observed to decolorize in 10 seconds (compared to 3-5 minutes taken to observe the color change of a Scott® paper towel saturated with MH according to one of the previous examples). Higher sensitivity to the odor was thus observed by inkjet printing the indicating agent onto the substrate.

Example 5

Figure 2:
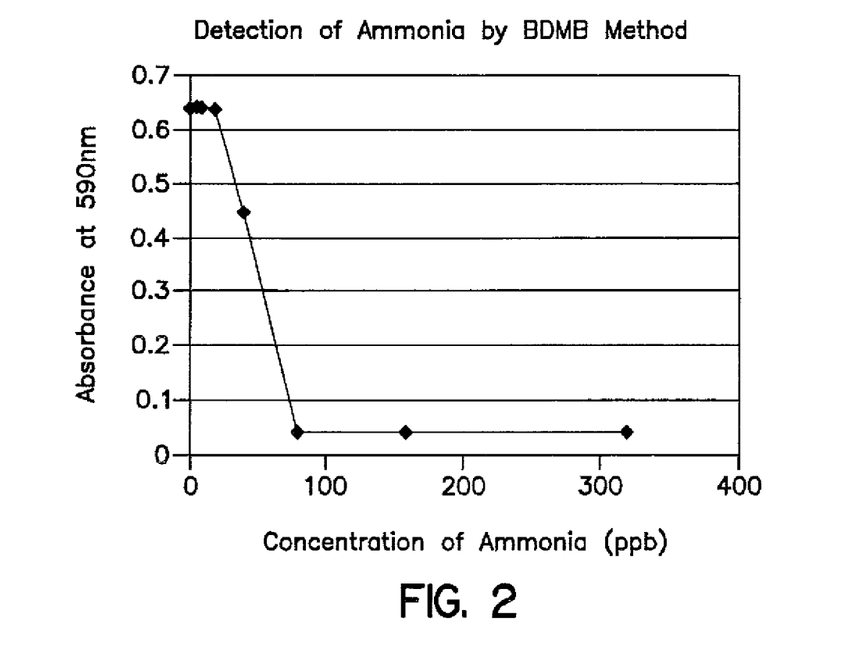
FIG. 2 shows a standard curve for the detection of ammonia by MH-dye.

As shown in FIG. 2, a standard curve was derived using ammonium hydroxide solution as an ammonia odor source in order to determine whether MH is a suitable indicating agent for ammonia.

Into each of 8 vials, 50 µl of a specific concentration of ammonia solution (0, 0.01, 0.02, 0.04, 0.08, 0.16, 0.32, and 0.64%, respectively) was mixed with 150 µl of MH solution (20 µl of 10.0 mg/ml MH in $CH_3CN$ with 5.0 ml of 40 mM sodium acetate and 4 M guanidine HCl, pH 5.1) and the vials were sealed and incubated for less than 4 min.

The solutions were then transferred to microtiter plate wells and the absorbances were measured at 590 nm. The absorbance readings were plotted against the concentrations of ammonia solutions, with the concentrations being represented as parts per billion (ppb). In FIG. 2, the x-axis is the concentration of ammonia in parts per billion (ppb) from 0 to 400 and the y-axis is the absorbance at 590 nm from 1 to 0.7. The sensitivity of MH to ammonia was very high, and it was shown that the sensitivity could be altered by varying the MH-dye concentration.

Example 6

Figure 3:
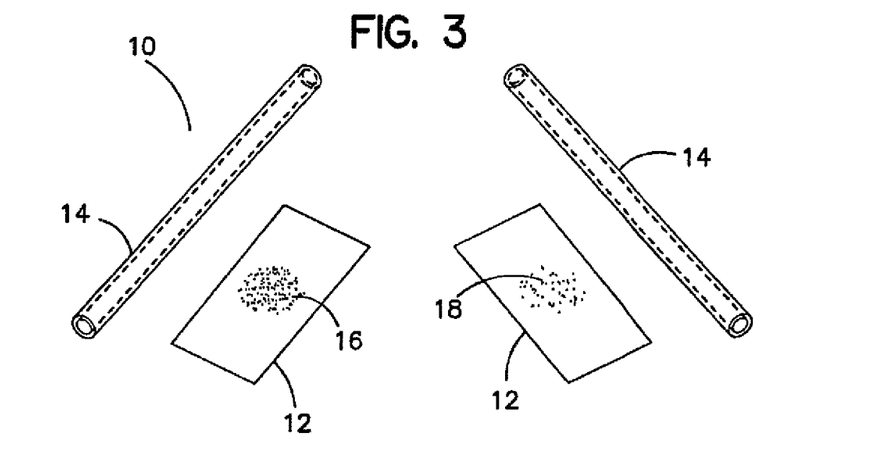
FIG. 3 shows simple breath testing devices according to one embodiment of the invention in an unassembled state, and a color change of the indicating agent in response to bad breath (right)
Figure 4A:
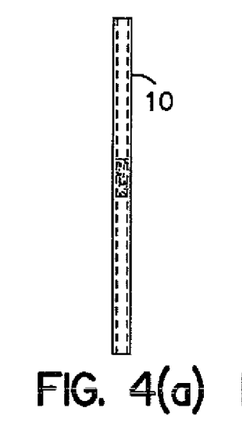
FIG. 4 shows the simple breath testing devices of Example 8, where the control tubes (a) and (e) have not been exposed to odor and tubes (b) to (d) have been exposed to breath odor (Tube (b): exposed to breath odor at BreathAlert™ detector reading of 2; Tubes (c) and (d): exposed to breath odor at BreathAlert™ detector reading of 3)
Figure 4B:
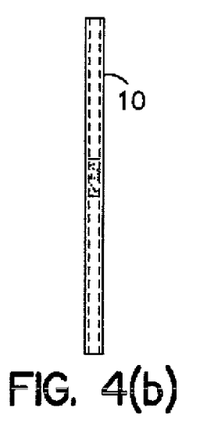
Figure 4C:
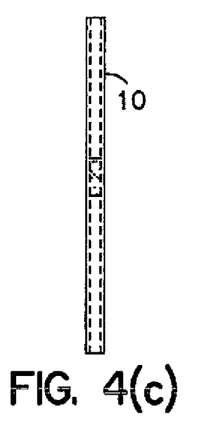
Figure 4D:
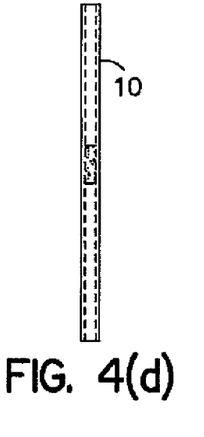
Figure 4E:
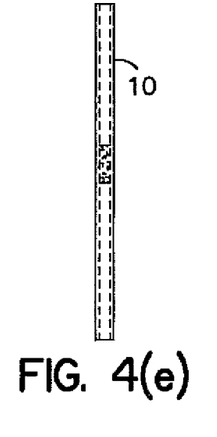

As shown in FIG. 3, breath testing devices 10 were made using a simple drinking straw into which a rolled dye-coated paper towel was inserted. The dye content on the paper towel varied depending on the sensitivity required for bad breath testing. Accordingly, 1 mg/ml stock solution of MH-dye 16 was applied on a Snowtex™-O nanoparticle-coated Scott® paper towel and allowed to air dry. The dye-coated paper towel was then cut into 2 cm×4 cm strips 12 which were rolled up and each strip 12 was inserted into a clear plastic drinking straw 14 from Glad Products Company of Oakland, Calif.

The breath testing devices 10 were tested by injecting known concentrations of ethyl mercaptan into the straws 14 to determine their sensitivity to sulphur odors. A color change 18 was noticed and was clearly visible in the presence of sulphur odors.

Several volunteers were also given a number of these straws and were asked to blow into them with one lung-full of breath. The tubes demonstrated bad breath sensitivity, typically with morning breath or after a spicy meal. Color change of the indicator articles was easily observable with an unaided eye, and the color intensities (L*a*b*) were measured using a handheld Minolta spectrophotometer from Minolta Co. Ltd, Osaka, Japan, Model #CM-2600d. An example of the data obtained from one sample is shown in Table 3 below.

TABLE 3

Color intensities of indicating article into which a person with bad breath has blown (expt.) compared with a control article which has not been exposed to bad breath

| SAMPLE | L | a* | b* | Δ E |
|---|---|---|---|---|
| Control | 66.32 | 7.27 | −38.98 | — |
| Expt. | 74.42 | −9.51 | −26.69 | 22.7 |

Example 7

The simple breath testing devices were tested in a laboratory by having volunteers test their breath using the breath testing devices described in Example 6, a clinical Halimeter™ breath tester and a BreathAlert™ breath tester.

Each volunteer first blew into the Halimeter™ and BreathAlert™ breath testers, and then blew through the visual breath indicating devices twice, each time with a full lung-full of breath.

The visual indicator devices containing the Michler's hydrol showed different degrees of decolorization of the blue dye. This could be read by the spectrophotometer and the color change measured by comparison of the before- and after-exposure samples was expressed as ΔE (the human eye can only distinguish between samples having differences in ΔE of 3 or greater).

The analytical readings taken from the Halimeter™ and BreathAlert™ breath testers were then compared to the color change of the straw. The results are shown in Table 4 below.

TABLE 4

Comparison of Halimeter ™, BreathAlert ™ and visual indicator devices of example 6

| SAMPLE | Color Change of Indicator Tube (ΔE) | BreathAlert ™ Handheld Meter Reading | Halimeter ™ Reading For Sulfur (ppb) |
|---|---|---|---|
| Control | 0.0 | — | 10 |
| Volunteer 1 | 3.0 | 1 | 37 |
| Volunteer 2 | 15.0 | 2 | 58 |

It should be noted that BreathAlert™ breath tester readings of 1 and 2 are low bad breath levels, hence the low hydrogen sulfide concentration readings from the Halimeter™ breath tester.

Example 8

Following on from the study of Example 7, a larger, more detailed study was conducted.

As in the previous study described in Example 7, volunteers were requested to blow into a BreathAlert T™ breath tester and then into two breath testing devices 10 as described in Example 6. This study obtained higher levels of bad breath than the previous study, and the results are shown below in Table 5. The breath testing devices used in the study are shown in FIG. 4.

TABLE 5

Correlation of color intensities (La*b*) of the indicator tubes with bad breath detector (BreathAlert ™) readings

| Tube # | Type of indicator tube | BreathAlert ™ reading | L value | a* value | b* value | ΔE value |
|---|---|---|---|---|---|---|
| a | Control | — | 60.84 | 13.04 | −46.93 | 32.1 |
|   |   |   | 63.01 | 9.83 | −44.91 | 27.8 |
| e | Control | — | 63.51 | 8.57 | −42.80 | 25.4 |
|   |   |   | 62.95 | 10.48 | −45.54 | 28.6 |
| — | Control | — | 62.15 | 9.87 | −43.75 | 27.5 |
|   |   |   | 62.09 | 9.99 | −43.84 | 27.6 |
| b | Sample | 2 | 71.34 | −0.17 | −32.33 | 10.3 |
|   |   |   | 70.13 | 1.66 | −34.44 | 13.2 |
| c | Sample | 3 | 71.92 | −2.49 | −30.81 | 7.5 |
|   |   |   | 72.72 | −2.69 | −28.65 | 6.54 |
| d | Sample | 3 | 71.06 | −4.44 | −30.71 | 6.18 |
|   |   |   | 70.51 | −2.36 | −33.58 | 9.53 |

The above color change readings, expressed as ΔE, show the sensitivity of the dye to the bad breath odor. The readings were calculated by comparing the sample to the white standard. Thus the larger the ΔE value, the more colored the sample. As the sample decolorizes on exposure to bad breath, the blue becomes paler in color and this is reflected in the smaller ΔE value, i.e. the color is moving closer to white. The human eye can distinguish between samples having differences in ΔE of 3 or greater. Thus, the eye can easily tell the difference between samples which had bad breath levels of 2 and 3 (as measured using the BreathAlert™ device), as well as the difference between the control and a sample having a bad breath of level 2.

As a result of this sensitivity, it is possible to produce a color scale which can inform the user of the intensity of his or her bad breath. For example, a panel on the side of a container containing the breath testing devices could include a color graduation scale, similar to the universal pH indicator. This scale would inform the user as to mild, moderate or intense bad breath readings.

The color-based technology was not found to give false negatives, unlike the electronic devices.

Example 9

KIMWIPES® tissues were coated with a 5% Snowtex-O® nanoparticle solution from Nissan Chemical and then air-dried. 5.0 mg/ml stock solution of MH-dye in acetonitrile was applied to the Snowtex-O® nanoparticle-coated KIMWIPES® tissues and a blue color was observed to develop as the applied dye solution dried.

Figure 5:
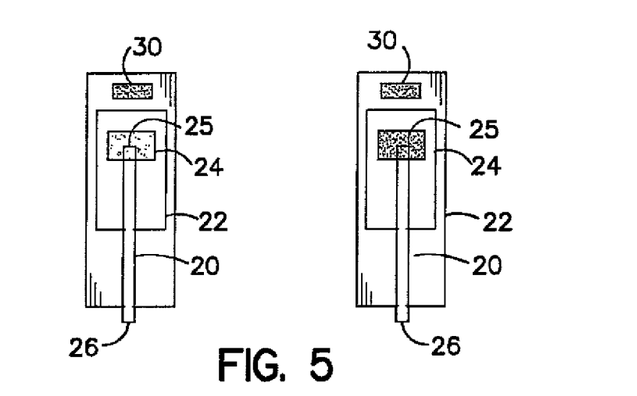
FIG. 5 shows a second embodiment of a breath testing device according to the invention with a color reference before (right) and after (left) exposure to bad breath odors.

As illustrated in FIG. 5, a drinking straw 20 from Glad Products Company of Oakland, Calif., was placed on a cardboard strip 22, and a piece of the dye-nanoparticle coated tissue 24 was placed over a first end 25 of the straw 20. Thus, when a person breathes into the second end 28 of the straw, their breath would pass through the tissue 24 at the first end of the straw. The straw was placed between two sheets of polyethylene 28 which were then heat-sealed so that only the second end 26 of the straw was exposed. A reference (or control) color strip 30 was also placed between the polyethylene sheets near, but separate from, the first end 24 of the straw and sealed when the polyethylene sheets were heat sealed. This reference strip was a piece of the dye-coated tissue and allows the user to compare the color of the strip over the first end of the straw with the reference strip to see if there has been a color change, and hence to determine whether he or she has bad breath (right). The reference strip could also include a scale of two or more shades of blue so that the user could compare the change of color of the tissue over the straw with the scale, and so determine the degree of his or her bad breath. For example, a slight change in the color could represent mild bad breath, a more pronounced fade to a lighter blue could represent medium bad breath, and a complete change from blue to colorless could represent very bad breath.

A simple study was carried out with 15 volunteers to test whether the bad breath testing device was suitable for indicating whether or not they had bad breath. The test was a simple "Yes" or "No", where a color change would indicate that the volunteer had bad breath ("Yes") and no color change would indicate that they did not have bad breath ("No").

Each volunteer was given 3 breath testing devices and was asked to breathe two full lung volumes into the second end of the straw first thing in the morning when getting out of bed (the most common time for bad breath). The volunteers were then asked to mark on the tube whether they thought they had bad breath.

Of the 45 devices which were handed out, 32 were returned and the results of this first test are shown in Table 6 below.

TABLE 6

Results from a test to determine the existence of bad breath using the breath testing article described above

| Volunteer Code | # Tested Samples | True Positive[a] | True Negative[b] | False Positive[d] (False Assumption[c]) | False Negative[e] (False Assumption[c]) |
|---|---|---|---|---|---|
| A | 3 | 2 | — | 1 | — |
| B | 3 | 3 | — | — | — |
| C | 3 | 2 | 1 | — | — |
| D | 2 | 1 | — | 1 | — |
| E | 3 | 1 | — | 2 | — |
| F | 2 | 2 | — | — | — |
| G | 3 | 2 | — | 1 | — |
| H | 2 | 2 | — | — | — |
| I | 3 | 1 | 1 | 1 | — |
| J | 3 | 2 | — | 1 | — |
| K | 2 | 1 | — | — | 1 |
| L | 3 | 3 | — | — | — |
| Total | 32 | 23 | 2 | 7 | 1 |

KEY:
[a] True Positive = Color change occurred when the user had bad breath.
[b] True Negative = No color change occurred when the user did not have bad breath.
[c] False Assumption = False assumption of the user
[d] False Positive = User did not believe they had bad breath when in fact they did.
[e] False Negative = No color change occurred when user believed they had bad breath.

These results indicate that the bad breath visual indicator devices are very sensitive and accurately inform the user of the presence of bad breath. Of the 32 devices tested, 22 showed a clear visual color change when the user thought they had bad breath. Interestingly, 7 color changes were recorded when the user did not think they had bad breath, but in fact they had bad breath. This finding matches the literature percentage of people who cannot detect their own bad breath: 22% of people in this study were unaware that they had bad breath, and the literature reports 25%. Only one breath testing device did not show a change in color when the user believed that they had bad breath.

Example 10

While the breath testing devices described in the previous examples were shown to be suitable for indicating the existence of bad breath, they were still believed to be slightly too large in size to be easily portable and to be able to be carried around discreetly. Further modifications to the breath testing devices were therefore made to miniaturize them further, in particular so that they were small enough so that several could fit into thin breath strip containers which could be carried in a pocket or handbag.

Figure 6:
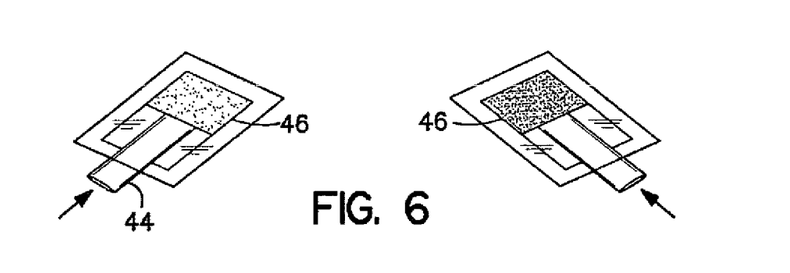
FIG. 6 shows a third embodiment of the breath testing device according to the invention.
Figure 7:
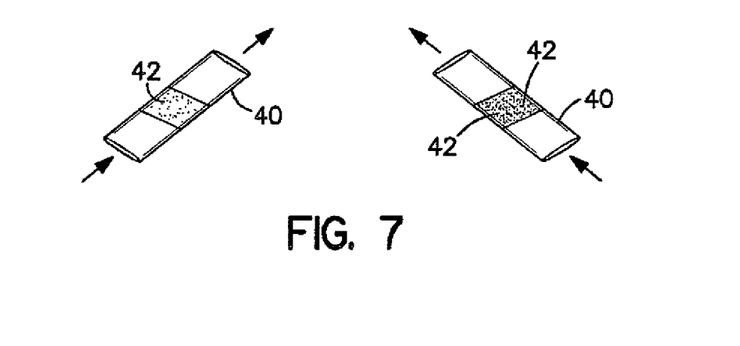
FIG. 7 shows a fourth embodiment of the breath testing device according to the invention.

Two miniaturized breath testing devices were therefore developed:

a) The first breath testing device (FIG. 7) was prepared by taking the article of example 8 (i.e. a drinking straw 40 into which a dye-treated tissue 42 had been inserted) and making the tube of the drinking straw shorter, for example, 4 cm long. The straw was then placed into a standard business card heated laminator (from Kinko's of Dallas, Tex.) so that the tube was flattened but air was still able to pass through the tube.

b) The second breath testing device (FIG. 6) was prepared by taking the article of example 9 (i.e. a drinking straw 44 having a dye-treated tissue strip 46 covering one end), and again cutting it to a length of approximately 4 cm. The straw was laminated as above.

Example 11

A dye-coated paper towel was attached to a 25 mm×50 mm strip of an adhesive-coated card material. The dye content on the paper towel varied depending on the sensitivity required for bad breath testing. Accordingly, 1 mg/ml stock solution of MH-dye was applied on a Snowtex®-O nanoparticle-coated Scott® paper towel and allowed to air dry, before being attached to the strip. A small straw was also placed onto the card and the device was packaged in a polyethylene film cover and the edges were heat sealed. A removable, peal-back polyethylene tab was then used to cover and temporarily seal the dye-coated paper towel. When the tab was pealed back and a user with bad breath exhaled onto the paper towel, the MH-dye turned colorless.

Example 12

Suitable dispensers for the breath testing devices were designed. These dispensers were relatively small, so that they could discreetly fit into a pocket, purse or handbag. Dispensers should also be inexpensive as the breath testing devices are intended to be disposable.

A small plastic rectangular dispenser (approximately 35 mm×60 mm×15 mm) which can hold about six breath testing devices of the type described in Example 10 was designed (FIG. 8), and a slightly larger dispenser for holding 12 breath testing articles is also envisaged. However, it should be clear that a dispenser could be sized to store any number of breath testing articles.

Figure 8:
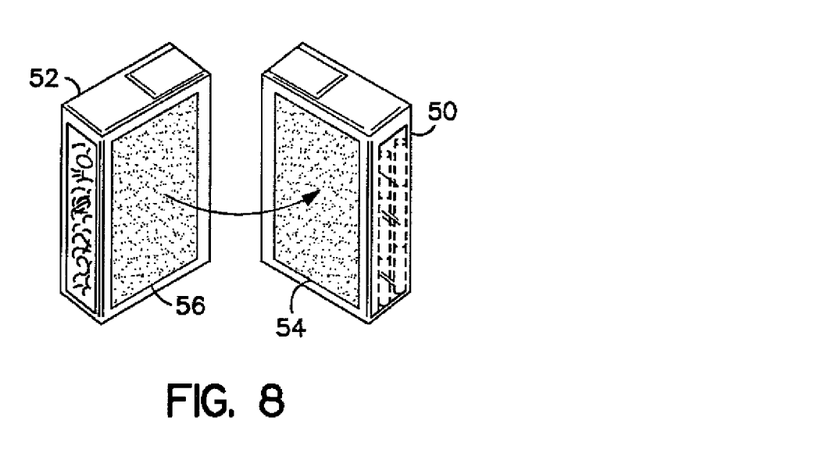
FIG. 8 shows a dispenser for the breath testing devices (right) which is attachable to a dispenser for breath mints (left)
Figure 9:
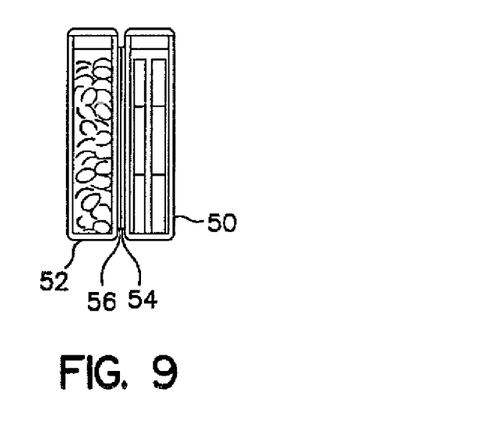
FIG. 9 shows the dispensers of FIG. 8 when attached to each other.

The dispenser 50 of this example was designed to be attachable to another dispenser 52 for breath mints, chewing gum, cigarettes or the like (FIG. 9). The dispensers are permanently attached to each other by means of a glue or double-sided tape in one embodiment. In an alternative embodiment, the dispenser 52 for the breath testing articles may have temporary attachment means, such as a magnet 54, or hook and loop fasteners (not shown) and can be attached to the second dispenser 52 as shown in FIG. 9, by means of an oppositely polarized magnet 56 attached to the other dispenser 52. Thus, the dispensers can be sold individually so that only one may be replaced at a time.

While the invention has been described in detail with respect to specific embodiments thereof, it will be apparent to those skilled in the art that various alterations, modifications and other changes may be made to the invention without departing from the spirit and scope of the present invention. It is therefore intended that the claims cover or encompass all such modifications, alterations and/or changes.

What is claimed is:

1. A breath testing device comprising a substrate and a visual indicating agent contained on the substrate, wherein the visual indicating agent is color sensitive to at least one odorous compound present in the breath of a user, wherein the visual indicating agent contains 4,4'-bis(dimethylamino)-benzhydrol, further wherein the substrate is configured to detect the odorous compound in a breath sample.

2. The breath testing device of claim 1, wherein the odorous compound contains sulfur.

3. The breath testing device of claim 1, wherein the odorous compound contains an amine.

4. The breath testing device of claim 1, wherein the substrate contains nanoparticles.

5. The breath testing device of claim 4, wherein the nanoparticles have an average length, width, height, and/or diameter of less than about 100 nanometers.

6. The breath testing device of claim 4, wherein the nanoparticles have a surface area of from about 50 to about 1000 square meters per gram.

7. The breath testing device of claim 4, wherein the nanoparticles include silica, alumina, or combinations thereof.

8. The breath testing device of claim 1, wherein the substrate contains a fibrous material.

9. The breath testing device of claim 8, wherein the fibrous material contains cellulosic fibers.

10. The breath testing device of claim 1, wherein the substrate is planar.

11. The breath testing device of claim 1, wherein the substrate is located within a passage of a carrier portion.

12. The breath testing device of claim 11, wherein the carrier portion is a cylindrical structure.

13. The breath testing device of claim 1, wherein the substrate covers an end of a carrier portion.

14. The breath testing device of claim 1, wherein the visual indicating agent is applied to the substrate as a solution.

15. The breath testing device of claim 14, wherein the concentration of the visual indicating agent is from about 0.001 to about 15% wt/wt.

16. The breath testing device of claim 1, further comprising a zone having a reference color, the reference color being the color to which the indicating agent will change upon exposure to the odorous compound.

17. A dispenser containing the breath testing device of claim 1.

18. The dispenser of claim 17, further comprising at least one breath freshener, wherein the breath testing device and breath freshener are contained in different compartments of the dispenser.

19. A breath testing device comprising a carrier portion defining a passage that is open at least one end, wherein the device contains visual indicating agent that is color sensitive to at least one odorous compound present in the breath of a user, wherein the visual indicating agent contains 4,4'-bis(dimethylamino)-benzhydrol.

20. The breath testing device of claim 19, wherein the substrate is located within a passage of a carrier portion.

21. The breath testing device of claim 20, wherein the carrier portion is a cylindrical structure.

* * * * *